United States Patent [19]
Cornier

[11] Patent Number: 6,042,552
[45] Date of Patent: Mar. 28, 2000

[54] DEVICE FOR COLLECTING ENDOMETRIAL FRAGMENTS

[75] Inventor: Edgard Cornier, Neuilly, France

[73] Assignee: Laboratoire C.C.D., Paris, France

[21] Appl. No.: 08/860,729

[22] PCT Filed: Nov. 27, 1996

[86] PCT No.: PCT/FR96/01881

§ 371 Date: Oct. 20, 1997

§ 102(e) Date: Oct. 20, 1997

[87] PCT Pub. No.: WO97/19642

PCT Pub. Date: Jun. 5, 1997

[30] Foreign Application Priority Data

Nov. 27, 1995 [FR] France ................................ 95 14018
Jun. 25, 1996 [FR] France ................................ 95 07852

[51] Int. Cl.$^7$ ................................................. A61B 10/00
[52] U.S. Cl. ........................ 600/562; 600/571; 604/22; 604/55
[58] Field of Search .................. 600/562, 564, 600/565, 570, 571; 604/22, 35, 54, 55

[56] References Cited

U.S. PATENT DOCUMENTS

| | | | |
|---|---|---|---|
| 3,088,454 | 5/1963 | Shute | 128/2 |
| 3,554,185 | 1/1971 | Kohl | 128/2 |
| 4,340,066 | 7/1982 | Shah | 600/564 |
| 4,620,548 | 11/1986 | Hasselbrack | 600/571 |
| 4,777,947 | 10/1988 | Zwick | 128/304 |
| 4,951,684 | 8/1990 | McMillan | 600/571 |
| 5,069,224 | 12/1991 | Zinnanti, Jr. | 600/571 |
| 5,131,402 | 7/1992 | Van Dooren | 600/570 |
| 5,476,104 | 12/1995 | Sheahon | 600/570 |
| 5,807,282 | 9/1998 | Fowler | 600/571 |

FOREIGN PATENT DOCUMENTS

| | | |
|---|---|---|
| 0 283 929 | 9/1988 | European Pat. Off. . |
| 2602414 | 2/1988 | France . |
| 3732582 | 4/1989 | Germany . |
| 1573819 | 8/1980 | United Kingdom . |

Primary Examiner—Cary O'Connor
Assistant Examiner—Charles Marmor, IV
Attorney, Agent, or Firm—Fisher, Christen & Sabol

[57] ABSTRACT

A device for collecting fragments of walls of internal organs. The device includes a tube having an opened proximal end, furthest from the patient, and a distal end sealed except for a suction aperture, a sealed plunger adapted to move in the tube and connected to the distal end of a rod having a proximal end, opposite to the patient, provided with a griping member and apparatus provided towards the distal end of the tube and adjacent to the suction aperture for enhancing and increasing the mechanical action of collection of the tube on the wall. The surface of the outer wall of the tube, adjacent to the aperture, over at least a part of the periphery of the wall, is rougher than the rest of the tube.

18 Claims, 2 Drawing Sheets

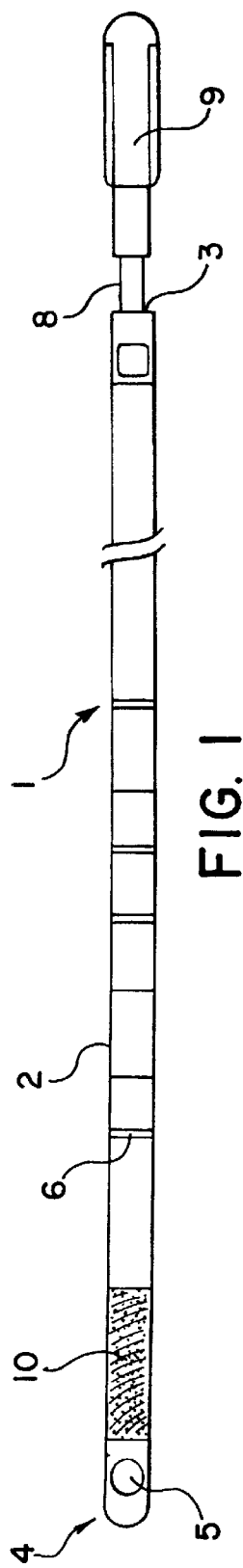
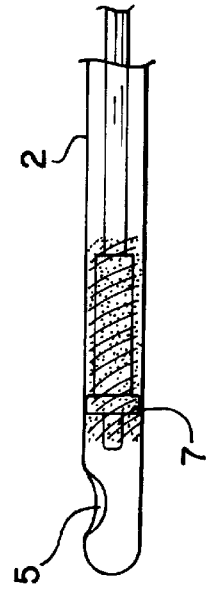
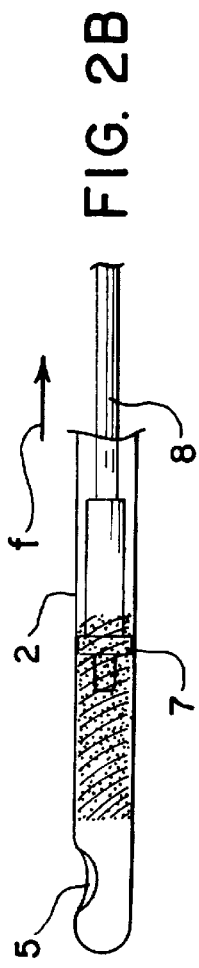
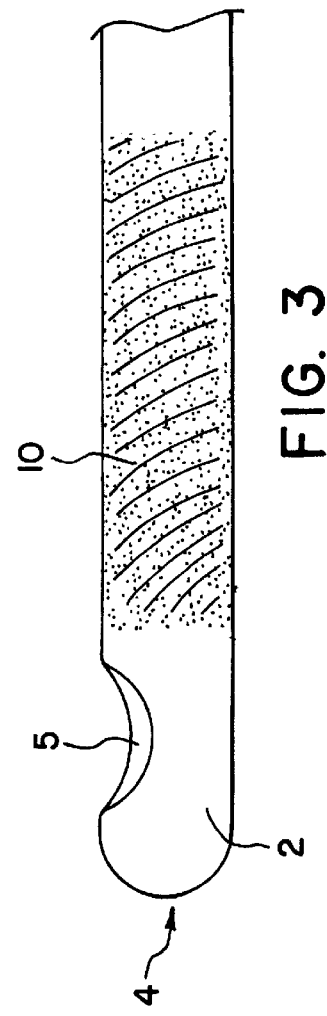

6,042,552

DEVICE FOR COLLECTING ENDOMETRIAL FRAGMENTS

BACKGROUND OF THE INVENTION

The present invention relates to a device for collecting fragments from the internal wall of the uterus, such as fragments of mucous membranes.

This type of device generally comprises a cylindrical tube, with an outer diameter of about 3 millimeters and an inner diameter of 1.5 to 2.6 millimeters, for a length of about 25 centimeters. The tube is open at a first end, the proximal end, and comprises at its opposite end, the distal end, an aperture, with a diameter of about 2 millimeters, called suction aperture and provided on the cylindrical wall of the tube, i.e. in a plane parallel to the longitudinal axis of the tube. A plunger fixed to the distal end of a rod is adapted to slide inside said tube, while the proximal end of the rod is fast with a gripping member.

This type of device is better known under the trade name PIPELLE DE CORNIER (Registered Trademark).

The generally single use of this known device is as follows: it is introduced through the patient's cervix up to the fundus uteri. Graduations provided on the tube make it possible to localize the arrival of the distal end of the tube, with the aperture, at the beginning of the uterine cavity. The operator, while holding the tube and pulling on the rod, by the gripping member, in the sense of removal with respect to the patient, produces a depression inside the tube and therefore a phenomon of suction at the level of the aperture disposed at the distal end of the tube. The collection of fragments of the uterine wall and of uterine mucous membranes is effected by displacing the tube, preferably by longitudinal reciprocating movement and rotation about the longitudinal axis, while maintaining the distal end of the tube against the wall. Fragments of mucous membrane are therefore torn from the wall and are sucked into the tube through the suction aperture. This latter, in side view, in a plane transverse to the axis of the tube, presents a concavity facing the outside of the tube. In other words, still in side view, the edges of the aperture form a dish whose concavity faces the outside of the tube.

Once the operation of collection is effected, the operator withdraws the device and then pours the contents of the tube resulting from the collections, into a recipient containing a histological fixing liquid.

It will be understood that this type of device must make it possible to collect fragments of uterine walls, mucous membrane, reliably and, of course, without pain. Likewise, the collection must be representative and therefore regular, in terms of depth, in a plane transverse to the wall. The collection must also be easy and rapid in order to shorten as much as possible the operation of collection, in view of the discomfort that it represents for the patient.

The known devices mentioned hereinabove are relatively satisfactory.

However, they are open to improvement and it is one of the objects of the present invention to propose an improved collection device presenting improved conditions of use, particularly in terms of reliability and of optimum conditions of collection, while respecting the required conditions recalled hereinabove.

SUMMARY OF THE INVENTION

To that end, according to the invention, the device for collecting fragments of walls of internal organs, such as the uterine wall, of the type comprising:

- a tube of which the proximal end, furthest from the patient, is open and of which the opposite distal end is sealed, except for a so-called suction aperture;
- a sealed plunger adapted to move in said tube and connected to the distal end of a rod whose proximal end, opposite to the patient, is provided with a gripping member;

is characterized in that means are provided at the distal end of the tube and adjacent to the suction aperture, for enhancing and increasing the mechanical action of collection of the tube from said wall.

The surface of the outer wall of the tube, adjacent to said aperture, over at least a part of the periphery of said wall, is preferably rougher than the rest of the tube.

Advantageously, the distal end of the tube presents a rough surface over the periphery of said tube and preferably over a length, in the longitudinal sense of the tube, included between 2 and 50 millimeters and preferably between 5 and 20 millimeters.

According to a first embodiment, the rough surface of the distal end of the tube is treated by friction with an abrasive material.

According to another embodiment, at least a part of the rough surface of the distal end of the tube is subjected to a chemical attack so as to create surface micro-porosities or equivalent, in order to attain the desired degree of roughness.

The surface treated with a view to increasing the roughness of the outer surface of the tube is advantageously disposed on the opposite side of the suction aperture with respect to the distal end of said tube.

BRIEF DESCRIPTION OF THE DRAWINGS

The invention will be more readily understood on reading the following description concerning an illustrative and non-limiting example, with reference to the accompanying drawings, in which:

FIG. 1 is a plan view of the collection device.

FIGS. 2A and 2B show the distal end of the tube for two different positions of the plunger; and FIG. 3 schematically shows the distal end of the tube on a larger scale.

DETAILED DESCRIPTION OF THE PREFERRED EMBODIMENTS

Figure 4:
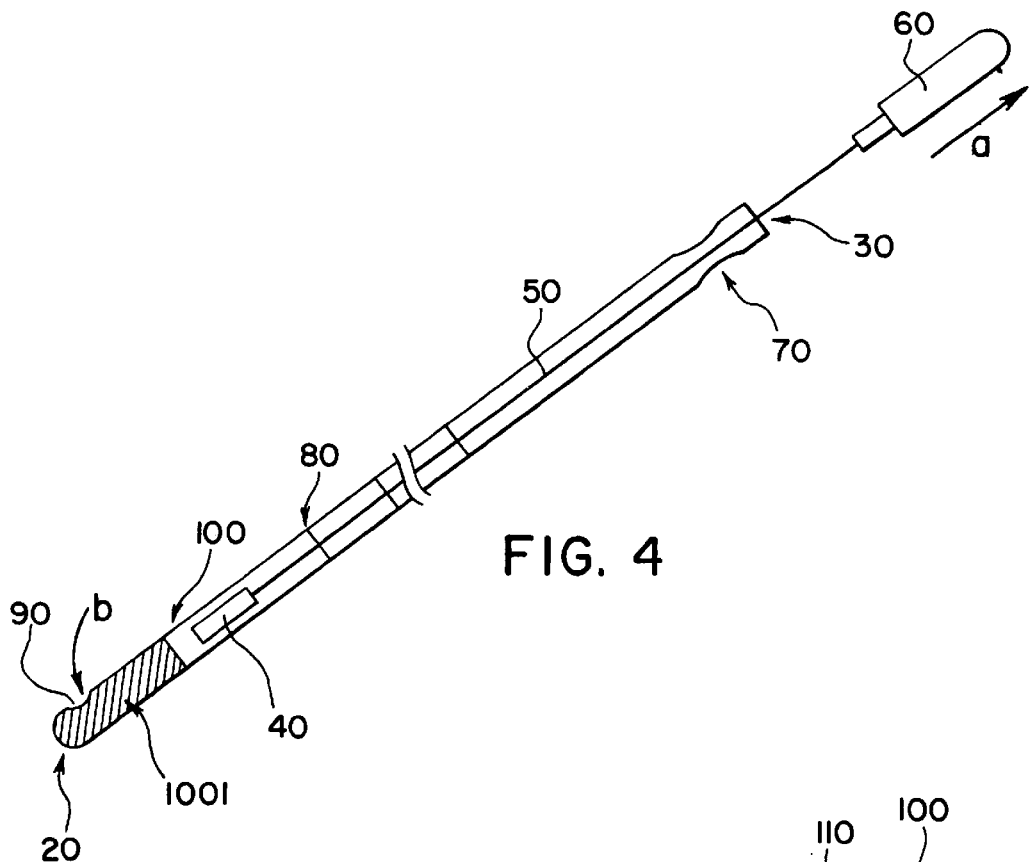

As shown in FIG. 1, the collection device bearing general reference 1 comprises a cylindrical tube 2, of circular base, and comprising an opening 3 at one of its ends, namely the proximal end, in other words the end furthest from the patient. The opposite end, or distal end, referenced 4, is sealed, except for a suction aperture 5, preferably of circular section.

The outer diameter of the tube 2 is included between 2 and 4 millimeters and, in a particular example, equal to 3.14 millimeters, and the inner diameter of the tube is 2.6 millimeters for example. Still by way of illustration, the tube presents a length of 20 to 30 centimeters, and for example 23.5 centimeters. The diameter of the hole is about 2 millimeters and preferably 2.1 mm.

The tube 2 comprises marks or the like, one of which bears reference 6, disposed in planes transverse to the longitudinal axis of the tube.

With reference to FIGS. 2A and 2B, there may slide inside the tube a plunger 7 in the form of a ring or washer, whose outer diameter is substantially equivalent to the inner diameter of the tube. The plunger 7 is fast with the distal end of a rod 8 of which the proximal end, towards the patient, is fast with a handle 9 (FIG. 1).

Starting from the starting position shown in FIG. 2A, the operator, while holding tube 2, pulls on the handle 9, in the direction of arrow f (FIG. 2B); the rod 8 and the plunger 7 are driven in the same direction, towards the patient. So doing, a depression is created at the level of the suction aperture 5.

The suction thus created at the level of aperture 5 entrains in the tube 2 the mucous membranes detached from the uterine wall where the device is introduced. The marks 6 make it possible, in known manner, to ensure that the distal end 4 has arrived at the beginning of the uterus. In conventional manner, the device is displaced in the uterine cavity by reciprocating movement of longitudinal direction, combined with a movement of rotation, in order to allow displacement of the suction aperture 5 with respect to the uterine wall from which the membranes are collected.

FIG. 3 shows an embodiment of the invention, on a larger scale, and more precisely the distal end part 4 of the tube 2 where the suction aperture 5 is located.

A zone 10 on the tube 2, shown hatched, corresponds to a particular surface state of the tube 2, on its outer wall. The surface state of this zone is such that it presents properties of roughness greater than the rest of the surface of the tube 2.

In zone 10, the tube 2 is preferably treated on the surface over a length of about 10 millimeters and, preferably still, over the whole periphery of the tube.

The surface treatment may be effected by scraping, polishing or any other similar operation, with the aid of an abrasive material, adapted to create micro-roughness or micro-pores. The rough zone 10 is preferably disposed adjacent to the suction aperture 5.

The rough surface state of the zone 10 may also be produced by chemical attack of the material constituting the tube 2.

The tube 2 is advantageously made of transparent plastics material, such as polypropylene. The plunger is made of EVA, while the rod 8 is for example made of supple acetal resin.

The device of the invention is preferably provided for single-use and may present any variation in terms of shape and dimensions, without departing from the scope of the invention.

"Single-use endometrial device"

The present invention relates to a single-use endometrial collection device.

Systematic screening of cancer of the cervix of the uterus by a smear has to a large extent enabled the mortality rate imputable thereto, to be reduced by promoting early diagnosis thereof.

To that end, gynecologists have for many years taken the habit of regularly watching over their patients by collecting cells at the level of their cervix, by scraping with spatulas, small sticks, cotton buds, . . . before spreading them on slides so as to allow analysis thereof.

However, such analyses do not always prove to be sufficient and, in particular, do not make it possible to detect or confirm a diagnosis of cancer of the endometrium. In fact, it is indispensable to that end to make collections at the level of the epithelial mucous membrane, therefore in the inner part of the uterine cavity, in particular, in order to allow a histological study.

For a long time, such collections could only be carried out by curettage under general anaesthetic. A single-use device, especially adapted for such collections, is known and used by practitioners.

This device, known under the name of "Pipelle de Cornier" is schematically constituted by a supple, smooth collection tube intended to be introduced in the uterine cavity and by a plunger mobile inside this tube and connected by a rod to an actuation knob projecting via the open proximal end of the tube. The closed, rounded distal end of this tube, whose diameter is of the order of 3 mm, is pierced with a lateral orifice and as a general rule with a lateral orifice of about 2 mm diameter; this orifice allows the suction, in the inner part of the tube, of the endometrial mucous under the action of the depression created by a displacement of the plunger in the direction of the proximal end, further to the practitioner pulling the actuation knob.

The mucous thus torn away is introduced in the inner part of the collection tube then transferred, after extraction from the device, into a flask containing a conservation liquid, with the aid of the plunger after the tube is cut at the level of its distal end, and this with a view to histological study thereof Despite its certain advantages, this device presents the drawback of not making it possible to scrape the endometrial coating when the uterine mucous is not detached, as is the case when an atrophy exists or when the patient has reached menopause.

In order to overcome these drawbacks, it has also been proposed to add to the end of the endometrial collection device various types of brushes allowing scraping and detachment of the epithelial cells to allow cytological study thereof; however, the addition of such brushes presents the drawback of fragilizing the device and, in particular, of greatly increasing the diameter of the collection tube and consequently of being detrimental to the patient's comfort.

It is an object of the present invention to propose a single-use endometrial collection device of the type mentioned above, which is capable of overcoming these drawbacks whilst making it possible to effect, parallel to the usual histological collection, a collection for cytological purposes which will complete the latter when it is not possible to detach the uterine mucous.

To that end, the invention concerns a single-use endometrial collection device, characterized in that the outer surface of the collection tube is rough at its distal end so as to allow a double collection by scraping of the epithelial cells at that level in addition to the histological collection.

According to the invention, the roughness preferably extends over the whole periphery of the distal end of the collection tube, and this over a length of about 1 to 1.5 cm. Such roughness may advantageously be obtained by an operation of grinding at that level of the material, as a general rule, plastics material, constituting the collection tube.

The fact of rendering rough, in particular of grinding, the distal end of the collection tube (sic) makes it possible to create a friction capable of detaching the epithelial cells; the cells thus detached may then be sucked under the effect of a depression induced by the plunger then spread on a slide so as to obtain a cytological endometrial collection comparable to a smear of the cervix of the uterus; the cells remaining attached to the rough zone may also be analyzed.

With the foregoing in mind, the essential advantage of the endometrial collection device according to the invention, which is totally painless for the patient when used, is therefore to allow both a histological collection and a cytological collection; in fact, after the collection tube has been cut at its distal end with the aid of scissors, the contents thereof may either be spread on a slide if the collection is for cytological purposes, or be placed in a conservation liquid if the collection is for histological purposes, or both, by spreading the ground part on slides for cytological purposes after having driven the contents from the tube with the aid of the plunger, for histological study.

The characteristics of the endometrial collection device forming the subject matter of the invention will be described in greater detail with reference to the accompanying drawings, in which:

FIG. 4 shows the device.

Figure 5:
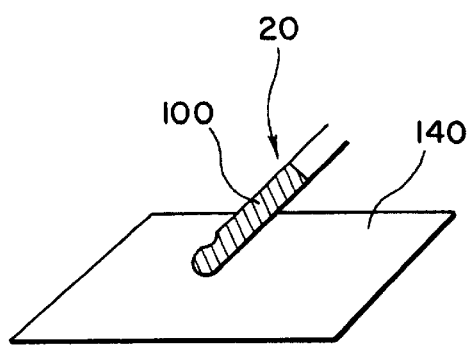
Figure 6:
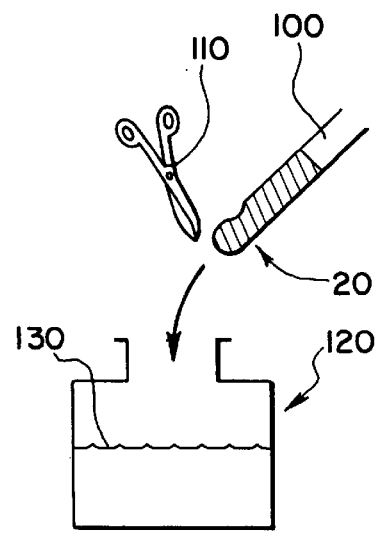

FIGS. 5 and 6 are diagrams showing how various types of analysis may be made from such a device.

According to FIG. 4, the device is essentially constituted by a collection tube 100 made of a supple and smooth transparent material and having a length of the order of 23 cm and a diameter of the order of 3 mm.

This tube 100 presents a rounded, closed distal end 20 by which it is intended to be introduced in the uterine cavity, and an open proximal end 30.

A plunger 40, measuring about 1 cm in length, may slide in the inner part of the collection tube 100. This plunger 40 is connected by a rod 50 to an actuation knob 60 projecting through the open proximal end 30 of the tube so as to allow the practitioner to displace the plunger 40.

A flattened part 70 provided at the proximal end 30 of the tube 100 prevents any untimely emergence of the plunger 40.

Marking graduations 80 located on the periphery of the collection tube 100, in particular at 4, 5, 6, 7, 8, 9 and 10 cm from its distal end 20, make it possible to measure the depth of the uterus.

The distal end 20 of the tube 100 is, futhernore, provided with a lateral suction aperture 90 measuring about 2 mm in diameter, as well as with a ground part 1001 extending over a length of 1 to 1.5 cm over the whole periphery of the collection tube 100. This ground part 1001 is shown hatched in the Figures.

The modus operandi of this device is as follows:

After disinfection of the cervix of the uterus and apart from the usual contraindications such as, pregnancy or infection, the collection tube 100 is pushed gently up to the fundus uteri. It should be noted that the passage of the cervix is usually painless for the patient. Prior to this introduction, the practitioner may, if need be, bend the tube in order to pre-curve it.

During introduction, the plunger 40 must be located at the level of the distal end 20 of the tube 100.

When the latter has been placed at the fundus of the uterine cavity, the practitioner creates a depression by pulling on the actuation knob 60 in the direction of arrow a and subsequently displacing the plunger 40 towards the proximal end 30 of the tube 100.

Tissular fragments detached from the endometrium may thus be sucked in the direction of arrow b in the inner part of the tube 100.

When this first phase has been effected, the practitioner displaces the tube 100 by circular, helicoidal movements from the fundus to the edge of the uterus, with the result that the ground part 1001 exerts an action of friction and of circular scraping capable of detaching epithelial cells; these may then be sucked in the inner part of the tube 100 under the action of the depression induced by the plunger 40; a function of scraping of the epithelium is therefore added to the histological collection by suction and detachment of the uterine mucous.

The practitioner then withdraws the tube 100 from the uterus and cuts it at the distal end 20 with the aid of scissors 1 10, as schematically shown in FIG. 6. The contents of the tube are then driven with the aid of plunger 40 from the actuation knob 60, and are either introduced in the direction of arrow A in a flask 120 containing a conservation liquid 130 when the collection is for histological purposes, as shown in FIG. 6, or spread out on a slide if the collection is for cytological purposes.

The invention also allows these two types of analysis to be made at the same time, by driving the inner part of the tube 100 in a flask 120, as shown in FIG. 6, and spreading the outer ground part 1001 on a slide 140 as shown in FIG. 5, in a manner largely comparable with that for making smears of the cervix of the uterus.

I claim:

1. A device for collecting fragments of walls of internal organs, the device comprising:

a tube having an open proximal end and a sealed distal end including a suction aperture;

a sealed plunger adapted to move within said tube, said plunger connected to a distal end of a rod, the rod including a gripping member at a proximal end thereof; and means for enhancing and increasing mechanical action of collection provided towards the distal end of the tube and adjacent to the suction aperture, said means comprising a rough surface disposed over at least a part of the periphery of an outer wall of the tube, wherein said rough surface is rougher than the rest of the tube.

2. The device according to claim 1, wherein said rough surface extends longitudinally over a length of a periphery of an outer wall of the tube, said length included between 2 and 50 millimeters.

3. The device according to claim 2, wherein said rough surface is made by rubbing the tube with an abrasive material.

4. The device according to claim 3, wherein said rough surface is disposed on the opposite side of the suction aperture with respect to the distal end of said tube.

5. The device according to claim 2, wherein said rough surface is made by chemical attack, so as to create micropores on the surface, in order to attain a desired degree of roughness.

6. The device according to claim 5, wherein said rough surface is disposed on the opposite side of the suction aperture with respect to the distal end of said tube.

7. The device according to claim 2, wherein said rough surface is disposed on the opposite side of the suction aperture with respect to the distal end of said tube.

8. The device according to claim 1, wherein said rough surface extends longitudinally over length of a periphery of an outer wall of the tube, said length extending between 5 and 20 millimeters.

9. The device according to claim 8, wherein said rough surface is disposed on the opposite side of the suction aperture with respect to the distal end of said tube.

10. The device according to claim 8, wherein said rough surface is made by chemical attack, so as to create micropores on the surface, in order to attain a desired degree of roughness.

11. The device according to claim 8, wherein said rough surface is made by rubbing the tube with an abrasive material.

12. The device according to claim 11, wherein said rough surface is made by rubbing the tube with an abrasive material.

13. The device according to claim 1, wherein said rough surface is made by chemical attack, so as to create micropores on the surface, in order to attain a desired degree of roughness.

14. The device according to claim 1, wherein said rough surface is disposed on the opposite side of the suction aperture with respect to the distal end of said tube.

15. A single-use endometrial collection device comprising:

- a supple, smooth collection tube adapted to be introduced into the uterine cavity of a patient;
- a plunger, mobile inside said tube and connected by a rod to an actuation knob projecting from an open proximal end of the tube;
- a closed, rounded distal end of said tube being pierced with an orifice, said orifice allowing suction of endometrial mucous under the action of a depression created by a displacement of the plunger in the direction of the proximal end; and
- means for enhancing and increasing mechanical action of collection provided towards the distal end of the tube and adjacent to said orifice, said means comprising a rough outer surface disposed over the distal end of the tube, the rough outer surface allowing collection by scraping of epithelial cells.

16. The device according to claim 15, wherein the orifice allowing the suction of the endometrial mucous is pierced laterally at the distal end of the collection tube.

17. The device according to claim 16, wherein the rough outer surface extends over the entire periphery of the distal end of the collection tube for a length of about 1 to 1.5 cm.

18. The device according to claim 17, wherein the collection tube is made of a smooth plastics material and is provided at said distal end with a rough outer surface obtained by an operation of grinding.

* * * * *